United States Patent [19]

Giannoble

[11] Patent Number: 6,152,911
[45] Date of Patent: Nov. 28, 2000

[54] VENOUS RETURN CATHETER HAVING MULTIPLE HELICAL SUPPORT MEMBERS

[75] Inventor: Jill W. Giannoble, Plano, Tex.

[73] Assignee: Chase Medical, Inc., Richardson, Tex.

[21] Appl. No.: 09/141,079

[22] Filed: Aug. 27, 1998

[51] Int. Cl.[7] .............................................. A61M 25/00
[52] U.S. Cl. .......................................... 604/524; 604/264
[58] Field of Search ..................................... 604/158, 280, 604/281, 282, 523–27, 532, 264; 600/433–35

[56] References Cited

U.S. PATENT DOCUMENTS

| | | | |
|---|---|---|---|
| 3,674,033 | 7/1972 | Powers | 128/350 R |
| 4,402,684 | 9/1983 | Jessup | 604/264 |
| 4,596,548 | 6/1986 | DeVries et al. | 604/4 |
| 4,639,252 | 1/1987 | Kelly et al. | 604/282 |
| 5,041,084 | 8/1991 | DeVries et al. | 604/43 |
| 5,069,674 | 12/1991 | Fearnot et al. | 604/282 |
| 5,074,849 | 12/1991 | Sachse | 604/280 |
| 5,269,752 | 12/1993 | Bennett | 604/28 |
| 5,279,596 | 1/1994 | Castaneda et al. | 604/282 |
| 5,300,022 | 4/1994 | Klapper et al. | 604/35 |
| 5,314,418 | 5/1994 | Takano et al. | 604/282 |
| 5,334,169 | 8/1994 | Brown et al. | 604/282 |
| 5,336,191 | 8/1994 | Davis et al. | 604/165 |
| 5,342,325 | 8/1994 | Lun et al. | 604/272 |
| 5,344,399 | 9/1994 | DeVries | 604/96 |
| 5,356,388 | 10/1994 | Sepetka et al. | 604/164 |
| 5,358,493 | 10/1994 | Schweich, Jr. et al. | 604/264 |
| 5,364,357 | 11/1994 | Aase | 604/96 |
| 5,401,244 | 3/1995 | Boykin et al. | 604/53 |
| 5,405,338 | 4/1995 | Kranys | 604/282 |
| 5,407,435 | 4/1995 | Sachse | 604/170 |
| 5,423,764 | 6/1995 | Fry | 604/187 |
| 5,441,484 | 8/1995 | Atkinson et al. | 604/96 |
| 5,443,448 | 8/1995 | DeVries | 604/96 |
| 5,449,343 | 9/1995 | Samson et al. | 604/96 |
| 5,460,608 | 10/1995 | Lodin et al. | 604/96 |
| 5,462,523 | 10/1995 | Samson et al. | 604/30 |
| 5,466,225 | 11/1995 | Davis et al. | 604/165 |
| 5,569,219 | 10/1996 | Hakki et al. | 604/282 |
| 5,571,091 | 11/1996 | Davis et al. | 604/165 |
| 5,593,394 | 1/1997 | Kanesaka et al. | 604/282 |
| 5,599,325 | 2/1997 | Ju et al. | 604/282 |
| 5,605,162 | 2/1997 | Mirzaee et al. | 128/772 |
| 5,607,394 | 3/1997 | Andersen et al. | 604/102 |
| 5,634,895 | 6/1997 | Igo et al. | 604/21 |
| 5,653,696 | 8/1997 | Shiber | 604/267 |
| 5,658,251 | 8/1997 | Ressemann et al. | 604/102 |
| 5,662,607 | 9/1997 | Booth et al. | 604/96 |
| 5,674,197 | 10/1997 | Van Muiden et al. | 604/95 |
| 5,695,483 | 12/1997 | Samson | 604/282 |
| 5,702,372 | 12/1997 | Nelson | 604/264 |
| 5,769,828 | 6/1998 | Jonkman | 604/280 |
| 5,782,811 | 7/1998 | Samson et al. | 604/527 |
| 5,795,341 | 8/1998 | Samson | 604/282 |
| 5,873,865 | 2/1999 | Horzewski et al. | 604/523 |
| 5,947,940 | 9/1999 | Beisel | 604/523 |
| 5,984,908 | 11/1999 | Davis et al. | 604/523 |

*Primary Examiner*—Glenn K. Dawson
*Assistant Examiner*—Catherine Serke
*Attorney, Agent, or Firm*—Jackson Walker, LLP

[57] ABSTRACT

A venous return catheter suitable for use in an extracorporeal circuit having a helical support member supporting the catheter about venting openings. A two-stage catheter is provided with a plurality of proximal openings at the midsection thereof with a substantially rigid helical support member being defined thereabout to prevent collapse or kinking of the catheter about the proximal openings when bent or twisted. The catheter has a proximal helical support member and a distal helical support member reinforcing the catheter body therealong. The spacing of the substantially rigid helical support member about the proximal openings is sufficient to permit large proximal openings. The cross section diameter of the substantially rigid helical support member is greater than the cross section diameter of the proximal and distal support members. The three helical support members are continuous with one another to support the length of the catheter body. The more rigid helical support member maintains its shape when twisted or bent, and also maintains a sufficient lumen diameter within the catheter during bending to facilitate an adequate flow rate of venous blood. A single stage catheter has a spaced helical support member and venting openings at the catheter distal end, with a more closely spaced helical support member extending proximal thereof.

22 Claims, 3 Drawing Sheets

VENOUS RETURN CATHETER HAVING MULTIPLE HELICAL SUPPORT MEMBERS

FIELD OF THE INVENTION

The present invention is generally related to medical catheters, and more specifically to venous return cardiac catheters used to siphon blood from the inferior vena cava, the superior vena cava, and the right atrium of the heart during open-heart surgery for routing to an extracorporeal circuit.

BACKGROUND OF THE INVENTION

Use of catheters to administer fluids into and drain fluids out of the body has been a standard practice in medical procedures for years. Many such catheters are available and used as part of an extracorporeal circuit during open-heart procedures.

In a typical open-heart procedure, blood is bypassed from the heart and lungs to a heart lung machine which, in combination with an oxygenator, pumps and oxygenates the blood passing through the extracorporeal circuit. When bypassing the heart, blood is siphoned away from the right atrium and/or vena cava using a venous return (suction) catheter, oxygenated and returned to the aorta using an aortic arch (delivery) catheter. The distal end of the venous return catheter is usually placed in the right atrial appendage and into the inferior vena cava, while the proximal end of the catheter is attached to the tube feeding to a venous reservoir. The venous reservoir is placed at a lower level than the operating table to create a differential head pressure. This differential head pressure acts to siphon blood residing from the inferior vena cava, the superior vena cava, and the right atrium via the venous return catheter into the venous return reservoir. In some cases, an active suction is created by maintaining a vacuum in the venous reservoir. This would help to draw more blood using a smaller cannula.

During the open heart procedure, both the venous return catheter and aortic arch catheter are first introduced into the heart, specifically the right atrium and inferior vena cava of the heart, and the aorta, respectively. The catheters are then clamped to inhibit blood flow therethrough. When the patient is ready to be placed on the extracorporeal circuit, the catheters are connected to inlet and outlet ends of the extracorporeal circuit, respectively, while simultaneously releasing the clamps.

Periodically, during the open-heart procedure, the heart needs to be moved or adjusted by the surgeon. As the venous return catheter is already attached to the heart, there is a potential for the catheter to bend and kink, which can restrict blood flow therethrough and possibly create a dangerous and even life threatening situation. Therefore, the venous return catheter is usually structurally reinforced to prevent kinking.

Sometimes it is desired to utilize a two-stage venous return catheter having multiple sets of openings. A first set of openings at the distal end facilitates drawing blood from the inferior vena cava, whereby a second set of proximal openings facilitate drawing venous blood from the superior vena cava or right atrium of the heart. The second set of proximal venting openings are cumbersome in that the catheter needs to be reinforced about these proximal openings to prevent kinking, yet these proximal openings need to be sufficiently large to draw venous blood therethrough at a sufficient flow rate and pressure and thus reduce the area for reinforcement.

One prior art two-stage venous return catheter is disclosed in U.S. Pat. No. 4,639,252 to Kelley et al. This catheter has a continuous layer of reinforcement material surrounding the proximal drainage openings, these drainage openings being punched through the layer of reinforcing material. The distal portion of the catheter is reinforced with a spring, as is the proximal portion of the catheter proximal of the continuous layer of reinforcing material.

In U.S. Pat. No. 5,769,828 to Jonkman there is disclosed a two-stage venous return cannula with an expandable reinforcing member. The catheter is provided with an expandable reinforcing atrial basket that prevents the cannula from kinking or collapsing about the proximal set of openings. The atrial basket is formed by a plurality of spaced beams.

The two-stage venous return catheter of the '252 Kelley patent and the '828 Jonkman patent both have limitations in that when the catheter is accidentally twisted during the surgery about the proximal openings, the diameter of the lumen therein becomes reduced, thereby restricting venous blood flow therethrough. The device of the '252 Kelley patent may kink at the continuous reinforcement if substantially bent. The device of the '828 Jonkman patent can also kink at the expandable reinforcing member if bent, and may even keep the kinked shape when comprised of a metal material.

There is desired an improved reinforced two-stage venous return catheter having structure adequately reinforcing the proximal openings while maintaining its shape when the catheter is twisted during use and manipulation within the heart during surgery.

SUMMARY OF THE INVENTION

The present invention achieves technical advantages as a venous return catheter having a substantially rigid helical coil embedded within the catheter body about a plurality of openings. The invention has multiple embodiments.

In a first embodiment, a two-stage venous return catheter has a catheter proximal end and a catheter distal end reinforced with separate less rigid helical coils. The proximal helical coil and the distal helical coil each abut the more rigid helical coil, the more rigid helical coil extending about a proximal set of openings. The more rigid helical coil adequately reinforces the catheter body about the proximal openings when the catheter is bent or twisted, and does not restrict venous blood flow therethrough when twisted or bent. The rigid helical coil maintains it shape during twisting and bending, and is resilient to forces created during manipulation by the surgeon.

The two-stage venous return catheter is particularly suited for insertion into the right atrium and inferior vena cava of the heart. The catheter further has a plurality of distal openings at the catheter distal end suited to vent blood from the inferior vena cava. The proximal set of openings are defined a suitable distance from the distal set of openings to facilitate venting blood from the superior vena cava and the right atrium of the heart, respectively.

The two-stage venous return catheter comprises a catheter body extending between a proximal end and a distal end having a body wall defining a lumen therein. A first helical support member extends within and supports the catheter body wall at a midsection of the catheter body. This first helical support member defines a helical spacing in the catheter body between adjacent portions of helical support member. The catheter body further has a plurality of proximal openings defined through the catheter body in communication with the lumen, these proximal openings being defined along the helical spacing and defining a generally helical arrangement of openings.

The two-stage venous return catheter further comprises a second helical support member extending within the catheter body wall between the catheter body distal end and the first helical support member. Preferably, the second helical support member abuts the first helical support member to provide continuous support of the catheter body. The catheter has a plurality of distal openings at the catheter distal end defined distal of the second helical support member. The proximal openings and the distal openings are spaced from one another a suitable predetermined distance such that the distal openings are adapted to draw blood from the inferior vena cava, and the proximal set of openings are adapted to draw blood from the superior vena cava and/or right atrium of the heart.

The two-stage venous return catheter is further provided with a third helical support member extending within the catheter body wall between the first helical support member and the catheter proximal end. The third helical support member preferably abuts the first helical support member to provide continuous catheter body support. The first helical support member defined about the proximal openings is more rigid than the second helical support member and the third helical support member. Moreover, the first helical support member has adjacent segments spaced further from one another than the spacing between the adjacent segments of the second helical support member and the third helical support member. Preferably, the cross section diameter of the wire forming the first helical support member is greater than the cross section diameter of the wire forming the second helical support member and the wire forming the third helical support member. The diameter of the proximal set of openings preferably has the diameter of greater than 0.05". The catheter body is preferably comprised of plastisol. Each of the helical support members is preferably comprised of a metal material, such as stainless steel.

The two-stage venous return catheter further has a first diameter portion defined between the catheter distal end and the first helical support member. A second diameter portion is defined proximal of the first diameter portion with a transition portion being defined therebetween. The second diameter portion is greater than the first diameter portion. The first helical support member is defined in the second diameter portion of the catheter, and may be also be defined in the transition portion if desired. The diameter of the lumen is sufficient to facilitate venous blood flow therethrough from the superior vena cava and the inferior vena cava of the human heart when forming a portion of an extracorporeal circuit.

In a second embodiment, a single stage venous return catheter is ideally suited for insertion into either the superior vena cava or the inferior vena cava. The single stage catheter has a distal end supported by a first helical coil member having adjacent spaced portions with a set of distal openings defined therebetween. The proximal end of the catheter is supported by a second helical coil member having more closely spaced adjacent portions. The first and second helical coil abut one another, and may comprise one continuous coil if desired.

DESCRIPTION OF THE PREFERRED EMBODIMENT

Figure 1:
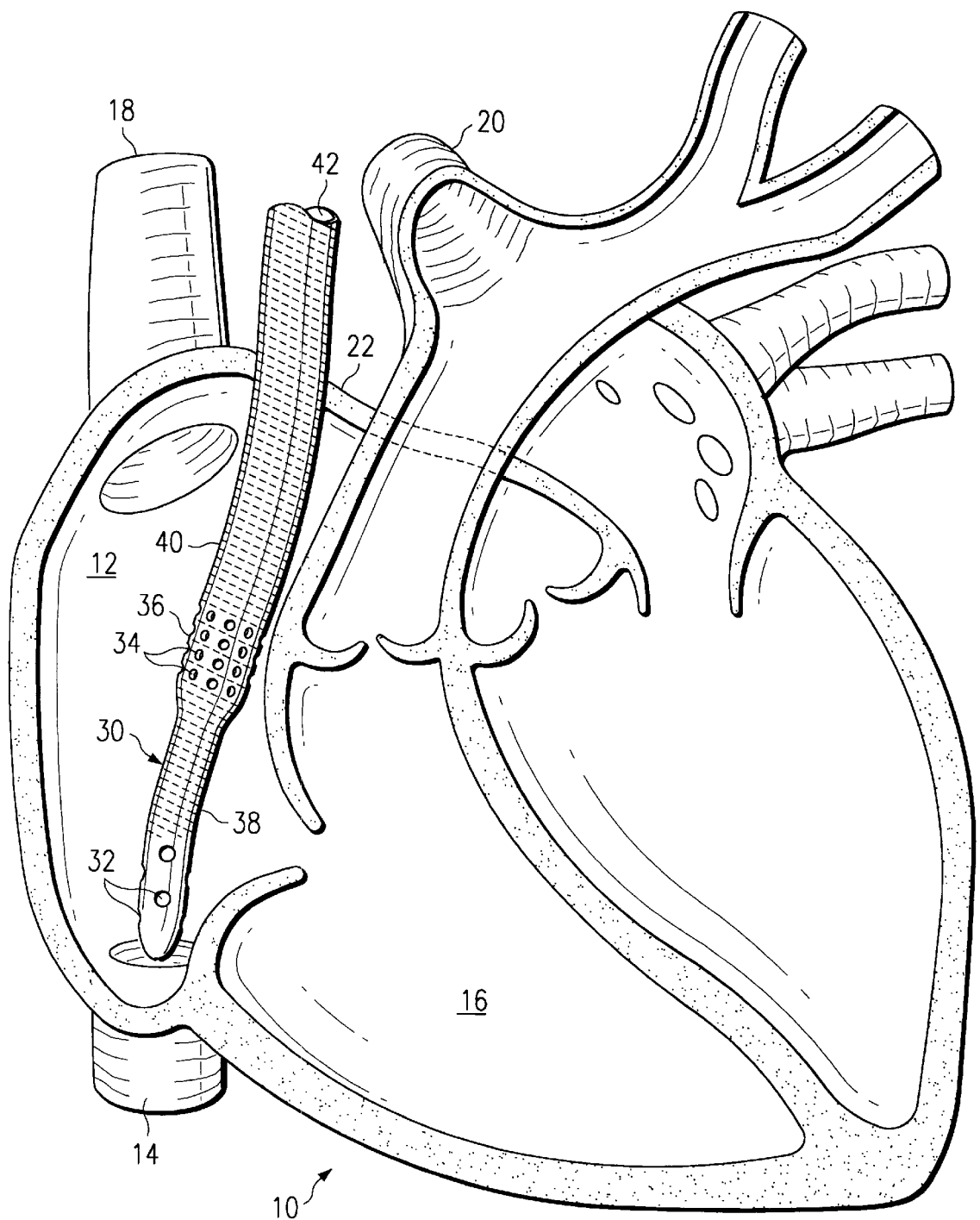
FIG. 1 is a sectional view of the human heart with the catheter of the present invention established in the proper position for drawing blood from the inferior vena cava and the right atrium of the heart.

Referring now to FIG. 1, there is shown a sectioned human heart 10 illustrating a right atrium 12 positioned above an inferior vena cava 14, and a right ventricle 16. The superior vena cava is shown at 18, and the pulmonary artery is shown at 20. As illustrated in FIG. 1, the normally shaped right atrium 12 has an atrial appendage generally shown at 22. This atrial appendage 22 is usually the most suitable location for a surgeon to form an incision for insertion of a venous return catheter 30 according to the preferred embodiment of the present invention.

Still referring to FIG. 1, the two-stage venous return catheter 30 according to a first embodiment of the present invention is shown in properly positioned into the heart 10. The catheter 30 is adequately supported along the entire length thereof to prevent kinking of the catheter during insertion, and during use thereof. The catheter 30 is shown to have a plurality of distal openings 32 positioned downwardly in the inferior vena cava 14 for drawing venous blood therefrom. The catheter 30 is further seen to have a second set of proximal openings 34 suitably spaced from the first set of openings 32 for drawing blood from the right atrium 12 of the heart and venous blood returning from the superior vena cava 18. Catheter 30 extends downwardly through and into the atrial appendage 22 via a small incision provided by the surgeon at an upper portion of the atrial appendage, as shown. As will be described in more detail shortly in reference to FIG. 2, catheter 30 is seen to have a first wire forming a substantially rigid helical support member 36 defined within the body wall of catheter 30 and about the plurality of proximal openings 34. The spacing of adjacent portions of the helical support member 36 is sufficiently large to define a helical spacing through which openings 34 are defined. Thus, the openings 34 are defined in the helical pattern between adjacent portions of the helical support member 36, as shown. The substantially rigid helical member 36 prevents the catheter from kinking when bent or twisted during use and insertion by the surgeon. The cross section diameter of the helical support member 36 is large enough to provide adequate reinforcement.

Catheter 30 is further seen to include a second wire forming a distal helical support member 38 and a third wire forming a proximal helical support member 40 integrally defined within the catheter body wall and reinforcing the respective portion of the catheter body. Together, the helical support members 36, 38 and 40 provide continuous support along the catheter body from closely adjacent the distal openings 32, about the proximal openings 34, and along the proximal portion of the catheter. The distal helical support member 38 and the proximal helical support member 40 have adjacent spiral portions more closely spaced to one another than the adjacent spiral portions of the substantially rigid helical support member 36, as shown. The cross section diameter of the second wire forming the distal helical support member 38 and the third wire forming the proximal helical support 40 also have a smaller diameter than the cross section diameter of the first wire comprising the more rigid helical support member 36. The distal support member 38 and the proximal support member 40 both adequately support the catheter body along the respective portion thereof due to the close spacing of the adjacent portions of the member, and also because the catheter body wall is continuous without openings. Openings 34 weaken the body member and thus require additional structural support. The larger helical support member 36 provides the adequate support about the midsection of the catheter about proximal openings 34 and prevents kinking, and also maintains a sufficient diameter of a lumen 42 extending therethough proximate openings 34 when bent to avoid restricting venous blood flow therethrough.

Figure 3:
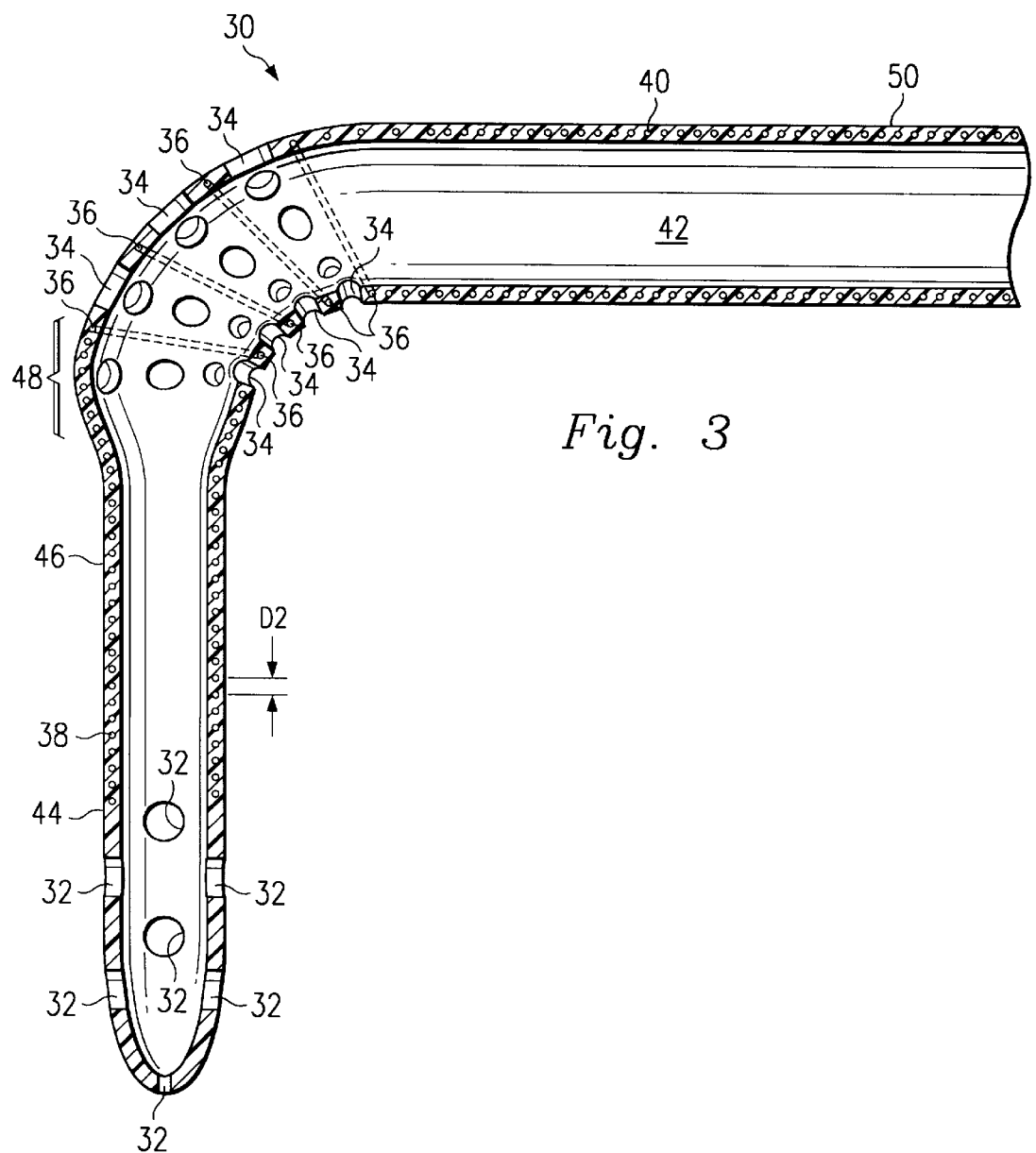
FIG. 3 is a sectional side view of the catheter of FIG. 2 illustrating the flow lumen maintaining its diameter when bent, with the proximal openings also maintaining an open position when bent.

The present invention achieves technical advantages in that large proximal openings 34 can be provided to facilitate venting blood from the right atrium and the superior vena cava of the heart, whereby the catheter is reinforced about the proximal openings 34 prevent kinking, and without reducing the diameter of the lumen 42 and most openings 36 when bent as shown in FIG. 3. The top openings 34 actually expand in diameter when the catheter tip is bent downwardly, as shown. Moreover, the substantially rigid helical support member 36 maintains its shape when twisted and does not become deformed. The helical support member 36 provides adequate flexibility and is not too rigid so as to inhibit positioning of the catheter within the heart by the surgeon as shown in FIG. 1. The catheter body has good consistent support along the length thereof as provided by the three helical support members continuously extending from the catheter distal end to the catheter proximal end as shown in FIG. 1.

Figure 2:
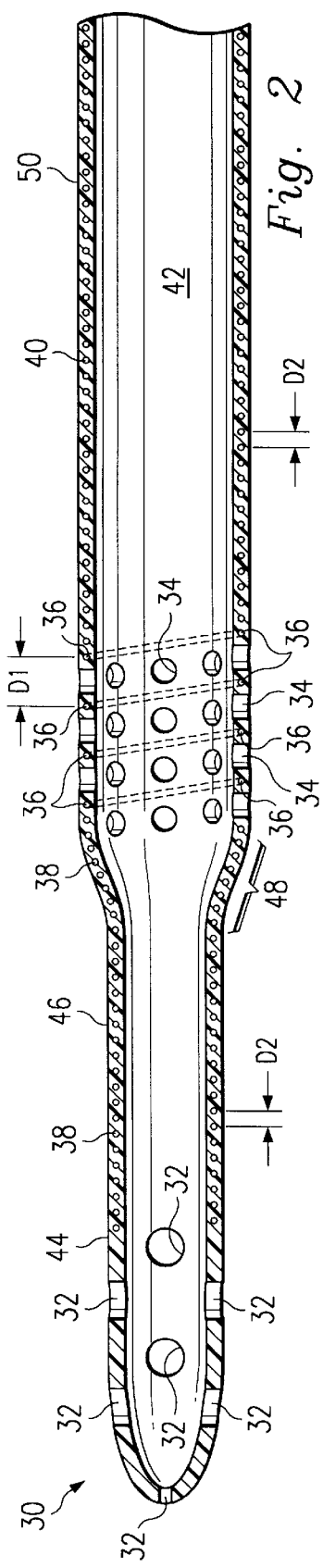
FIG. 2 is a sectional side view of the two-stage catheter of the present invention including a rigid helical support member defined about the proximal openings to prevent kinking of the catheter about the proximal openings.

Referring now to FIG. 2, there is shown a longitudinal cross section of the catheter 30 shown in FIG. 1. Catheter 30 is seen to have a catheter body 44 with the substantially rigid midsection helical support member 34, the distal helical support member 38, and the proximal helical support member 40 being integrally embedded within the walls of body 44. The catheter body 44 is seen to have a distal portion 46 having a first diameter from distal openings 32 to a transition portion shown at 48. Transition portion 48 tapers outwardly to a proximal portion shown at 50 having a larger diameter than the distal portion 46, as shown. This transition portion 48 in combination with the distal portion 46 and proximal portion 50 comprises the two-stage venous return catheter for the intended use shown in FIG. 1. As shown, the proximal plurality of openings 34 and helical support member 36 are defined within the proximal portion 50 and are closely proximate the transition portion 48.

Figure 4:
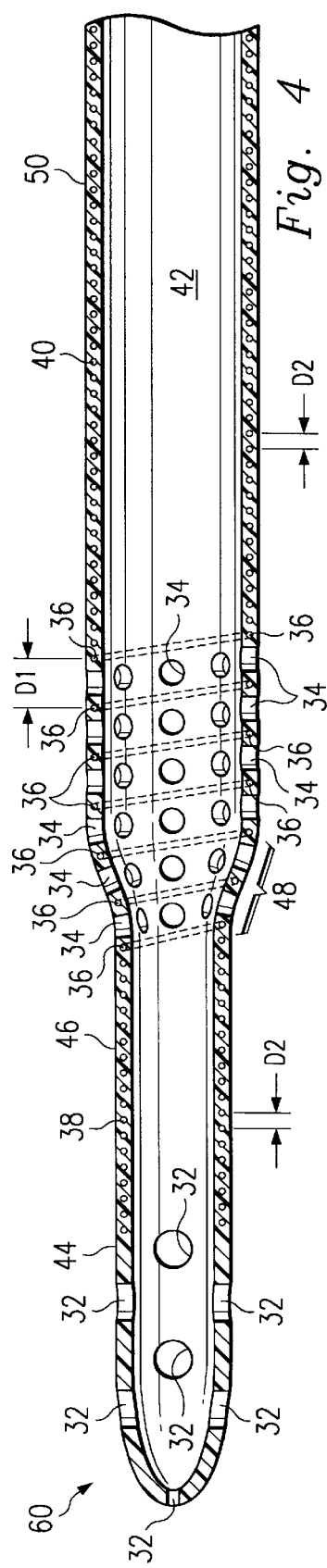
FIG. 4 is a sectional side view of an alternative embodiment of the two-stage catheter with the more rigid helical member extending a cross the transition portion.

In an alternative embodiment shown as catheter 60 in FIG. 4, the plurality of proximal openings 34 and helical support member 36 are defined over the transition portion 48, and extend across the both the transition portion 48 and the proximal portion 50 adjacent the transition portion 48.

As shown in FIG. 2, the spacing between adjacent spiral portions of the helical support member 36, identified as dimension D1, is substantially greater than the spacing between adjacent spiral portions of the distal support member 38 and proximal support member 40, shown as dimension D2. The larger dimension D1 defines a large helical spacing therebetween through which the plurality of large openings 34 are defined through the catheter body wall 44. Preferably, the diameter of openings 34 is at least 0.05".

Likewise, a suitable diameter of distal openings 32 is also about 0.05" to facilitate venting blood therethrough at a suitable rate and pressure from the inferior vena cava, the superior vena cava and the right atrium of the heart. The diameter of lumen 42 is sufficient to allow venous blood flow therethrough at a suitable rate and pressure to effectively bypass the venous blood flow returning to the heart and forming a portion of the extracorporal circuit.

The cross section diameter of the helical support member 36 is substantially larger than the cross section diameter of the distal support member 38 and the proximal support member 40. In the preferred embodiment of the present invention, the cross section diameter of the wire forming the midsection support member 36 is approximately 0.035", whereby the cross section diameter of the wire forming the distal support member 38 and the wire forming the proximal support member 40 is approximately 0.015". The smaller cross section diameter of the distal support member 38 and the proximal support member 40 is adequate since the adjacent spiral portions are more closely spaced, represented by distance D2, and the catheter body wall is continues therewith, as opposed to the perforated portion of the catheter body defined by the plurality of openings 34.

As shown in FIG. 2, the proximal end of support member 38 closely abuts the distal end of support member 36 to provide continuous reinforcement along the catheter body. Likewise, the distal end of support member 40 is seen to abut the proximal end of support member 36 to provide continuous support along the catheter body as well.

The catheter body 44 is preferably comprised of plastisol, polyvinylchloride or other suitable resilient materials that are conventional in the medical field. Catheter 30 is preferably manufactured by using a mandrel and dip process, whereby a mandrel is first dipped in the liquefied plastisol body material, the respective helical support members are then disposed thereabout, and then the catheter is dipped once again to complete the process and embed the helical support members therewithin. Thus, the present invention can be manufactured according to conventional processing techniques.

The two-stage venous return catheter of the present invention provides a substantially rigid helical support member about a plurality of proximal openings to provide adequate catheter support to prevent kinking, yet allows bending and twisting of the catheter body without damaging the support member and without significantly reducing the inner diameter of the lumen during use. Thus, an adequate venous blood flow rate can be maintained through the catheter during use without significant restriction when the catheter is manipulated within the heart. Adequate catheter body support is provided along the transition portion as well when the catheter body diameter transitions from one diameter to another diameter. Sufficiently large proximal openings are provided to vent blood at an adequate flow rate and pressure from inferior vena cava and the right atrium of the heart.

Figure 5:
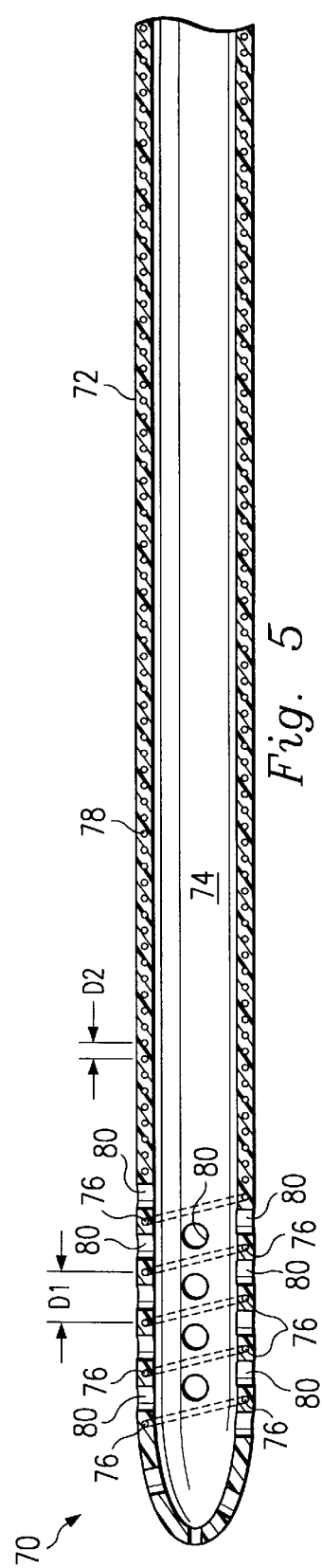
FIG. 5 is a sectional side view of a single stage catheter with a spaced helical member and openings at the catheter distal end.

Referring now to FIG. 5, there is shown a single stage venous return catheter 70 according to the second embodiment of the present invention. Catheter 70 is seen to have a body 72 extending from a distal end to a proximal end with a blood flow lumen 74 defined therethrough. Provided at the distal end of catheter body 72 is a coiled wire forming a helical support member 76 having spaced adjacent portions reinforcing the distal end of the catheter as shown. A second proximal helical support member 78 comprised of a second wire abuts the proximal end of the first helical support member 76 and extends proximally thereof to support the proximal portion of the catheter 70 as shown. Defined through body member 78 along the helical spacing between helical member 76 is a plurality of venting openings 80, as shown. The distal helical support member 76 adequately supports the distal end of the catheter 70 and is sufficiently spaced to accommodate the plurality of openings 80. The coiled helical member 76 prevents the distal end of catheter 70 from kinking within a body vessel, and maintains the nominal diameter of lumen 74 while keeping openings 80 open if bent or twisted. While two separate coiled members 76 and 78 are shown, the catheter could be reinforced along the length thereof by a single helical member comprised of a single wire extending along the length of the catheter 70, wherein the spacing between the adjacent members are increased at the distal end to accommodate the plurality of circumferentially spaced openings 80 as shown.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

What is claimed is:

1. A catheter, comprising:
   a catheter body extending between a proximal end and a distal end having a body wall defining a lumen therein; and
   a single first rigid helical support member extending within and supporting said catheter body wall of said catheter body, said first rigid helical support member defining a helical spacing in said catheter body between adjacent portions of said first rigid helical support member, said catheter body having a first plurality of openings defined through said catheter body in communication with said lumen, said first plurality of openings being defined along said helical spacing defining a generally helical arrangement.

2. The catheter as specified in claim 1 wherein said second rigid helical support member abuts said first rigid helical support member to provide continuous catheter body support.

3. The catheter as specified in claim 2 further comprising a second plurality of openings at said catheter body distal end defined distal of said second rind helical support member.

4. The catheter as specified in claim 3 wherein said first and second plurality of openings are spaced a first predetermined distance sufficient to facilitate drawing venous blood from the inferior vena cava and the right atrium of the human heart.

5. The catheter as specified in claim 3 further comprising a third rigid helical support member extending within said catheter body wall proximal of and not overlapping said first rigid helical support member.

6. The catheter as specified in claim 5 wherein said first rigid helical support member is more rigid than said third rigid helical support member.

7. The catheter as specified in claim 5 wherein said third rigid helical support member abuts said first rid helical support member to provide continuous catheter body support.

8. The catheter as specified in claim 7 wherein said first rigid helical support member comprising a first wire having a circular cross section, said second helical support member comprising a second wire also having a circular cross section, said first wire having a greater cross section diameter than a cross section diameter of said second wire.

9. The catheter as specified in claim 1 wherein said first rigid helical support member is more rigid than said second rigid helical support member.

10. The catheter as specified in claim 1 wherein a spacing between adjacent portions of the first rigid helical support member is greater than a spacing between adjacent portions of said second rigid helical support member.

11. The catheter as specified in claim 1 wherein said plurality of proximal openings have a diameter greater than 0.05".

12. The catheter as specified in claim 1 wherein said catheter body is comprised of plastisol.

13. The catheter as specified in claim 1 wherein said catheter body is comprised of polymeric material.

14. The catheter as specified in claim 1 wherein said first rigid helical support member is comprised of metal wire.

15. The catheter as specified in claim 1 wherein said second rigid helical support member is comprised of metal wire.

16. The catheter as specified in claim 1 wherein said catheter body has a first diameter portion between said catheter distal end and said first rigid helical support member, a second diameter portion proximal of said second rigid helical support member, and a transition portion therebetween, said second diameter being greater than the first diameter.

17. The catheter as specified in claim 16 wherein said first rigid helical support member is defined in said second diameter portion.

18. The catheter as specified in claim 16 wherein said first rigid helical support member is defined in said transition portion.

19. The catheter as specified in claim 1 wherein said catheter body lumen has a sufficient diameter to permit venous blood flow therethrough from the right atrium, the superior vena cava and the inferior vena cava of a human heart.

20. The catheter as specified in claim 1 wherein said first plurality of openings are defined at said catheter body distal end.

21. The catheter as specified in claim 1 wherein said first rind helical support member abuts said second rigid helical support member.

22. The catheter as specified in claim 1 wherein a spacing between adjacent portions of the first rigid helical support member is greater than a spacing between adjacent portions of said second rigid helical support member.

* * * * *